United States Patent [19]

Vice

[11] 4,028,810

[45] June 14, 1977

[54] ROOT CANAL FILE

[75] Inventor: Bobby C. Vice, Augusta, Ga.

[73] Assignee: Karl F. Kinkel, Augusta, Ga.

[22] Filed: Aug. 11, 1975

[21] Appl. No.: 603,470

[52] U.S. Cl. .................................................. 32/57
[51] Int. Cl.² ........................................... A61C 5/02
[58] Field of Search ................ 32/57, 60 R, 27, 26; 145/61 R; 279/42; 408/226

[56] References Cited

UNITED STATES PATENTS

| 2,016,766 | 10/1935 | Blair | 32/26 |
| 3,358,826 | 12/1967 | Siegel | 32/40 R |
| 3,855,705 | 12/1976 | Malmin | 32/40 R |
| 3,924,334 | 12/1975 | Lentine | 32/57 |

OTHER PUBLICATIONS

Silverman's Dental Catalogue, p. 37, 1976 Edition, Apollo Road, Plymouth Meeting, Pa. 19462.

*Primary Examiner*—Robert Peshock
*Attorney, Agent, or Firm*—Beveridge, DeGrandi

[57] ABSTRACT

An endodontic instrument for treating a pulp canal includes a handle portion adjustably mounted in telescoping relation on the shaft of an elongated working tool, with cooperating grooves in the shaft and handle preventing relative movement therebetween during use of the instrument. Means are provided for quickly and accurately adjusting the working length of the tool projecting from the handle and for quickly and reliably interlocking the tool and handle in the desired adjusted relationship with the end of the handle acting as a positive stop limiting the depth of penetration of the working tool portion during use of the instrument.

3 Claims, 6 Drawing Figures

ROOT CANAL FILE

BACKGROUND OF THE INVENTION

1. Field of the Invention

This invention relates to endodontic instruments for treating of pulp canals and to a means for accurately, reliably and quickly adjusting the working length of such instruments.

2. Description of the Prior Art

Root canal therapy on endodontically involved teeth routinely involves the removal of the pulp from the root canal. This is conventionally accomplished by initially drilling the tooth to the pulp chamber, then reaming the canal with an elongated thin file, reamer, broach, or the like instrument made from a high strength, resilient metal capable of sufficient flexing to following the normal curvatures of the root canal. In the use of these instruments, referred to generally hereinafter as root canal files, extreme care must be taken to avoid penetration beyond the root canal to avoid injury and possible infection of the adjacent periodontal tissue and bone structure. At the same time, it is important to remove all of the pulp tissue from the canal to avoid the possibility of involvement of the root canal and the adjacent periodontal tissue subsequent to completion of the root canal treatment.

The length of the tooth involved, as well as the length of the root canal, is accurately determined by means of X-rays, and various techniques and devices have been devised in the past for limiting the depth of penetration of the root canal files to the root tip. Thus, many dentists employ a stop member which is penetrated by the root canal file for the desired distance, with the stop member being positioned to engage the top of the tooth to limit penetration. However, these stop members, normally made of a semi-rigid thermoplastic material, are easily displaced, particularly in working within the limited area of a patient's mouth and considering the relatively small size of the instruments involved.

It has also been proposed to provide screw threads on the shaft of the file, with a nut threaded onto the file to act as a stop. Again, however, manipulation of the file within a patient's mouth can easily result in the nut being moved on the shaft.

Another device, in common use, comprises a metal handle having movable jaws which are clamped onto the shaft of the handle by a threaded nut in a chuck-like arrangement, with the end of the handle and the chuck nut acting as the stop member. However, tightening of the chuck with sufficient force to avoid slippage was not always accomplished, particularly since there is a tendency to tighten the very small nut of the chuck by finger pressure only rather than to use the very small wrench to tighten the nut. Also, movement of the chuck nut during tightening inherently produced a change in the projecting length of the working portion of the file, making accurate measurement of the tool difficult.

SUMMARY OF THE INVENTION

The foregoing and other disadvantages of the prior art are avoided according to the present invention which is characterized by providing a series of annular grooves or ridges around the shaft portion of a root canal file, which grooves cooperate with mating ridges or grooves within the jaws of a tightening chuck on a handle to firmly interlock the handle and root canal file in any desired adjustment position. The cooperating, interlocking ridges and grooves in the chuck and on the file shaft eliminate the necessity for tightening the chuck by wrench, thereby greatly facilitating the adjustment of the file in the handle.

The nut of the chuck is formed with flats on its outer surface adapted to fit closely within a groove in a length-adjusting tool and be held thereby so that rotation of the instrument handle will loosen or tighten the chuck on the shaft of the file. The length adjusting tool is provided with an elongated, narrow slot for receiving the file, and an adjustable stop is positioned in the groove to act as an abutment for the end of the file. A scale mounted along the groove is provided so that the adjustable stop can be positioned to accurately determine the length of the file which will project from the end of the nut when the nut is tightened in the tool.

To position a file in a handle, the tool is adjusted to the desired file length in accordance with measurements determined in accordance with standard procedure. Thereafter, with the chuck nut loose, the tool handle is telescoped onto the cylindrical shaft portion of the file and the nut is positioned in the tightening groove with the end of the nut abutting the end of the groove. The file is then telescoped through the handle until the end thereof abuts the stop within the file slot of the adjustment tool, and the handle is turned in a direction to tighten the nut. When the chuck is tightened sufficiently to engage the ridges and grooves on the chuck and file handle, further rotation of the handle will withdraw the nut from the end of the tightening slot. However, since the ridges and grooves are extremely shallow, only a relatively small movement is required to completely tighten the nut and, this small amount of movement can readily be determined and compensated for in the positioning of the scale on the tool. Thus, the file is quickly and easily fixed in the handle with only finger pressure being required to secure the file sufficiently to assure against unintentional movement during use of the instrument.

BRIEF DESCRIPTION OF THE DRAWINGS

The foregoing and other features and advantages of the invention according to the present invention will become more apparent from the following detailed description, taken in conjunction with the drawings in which.

DESCRIPTION OF THE PREFERRED EMBODIMENT

Figure 1:
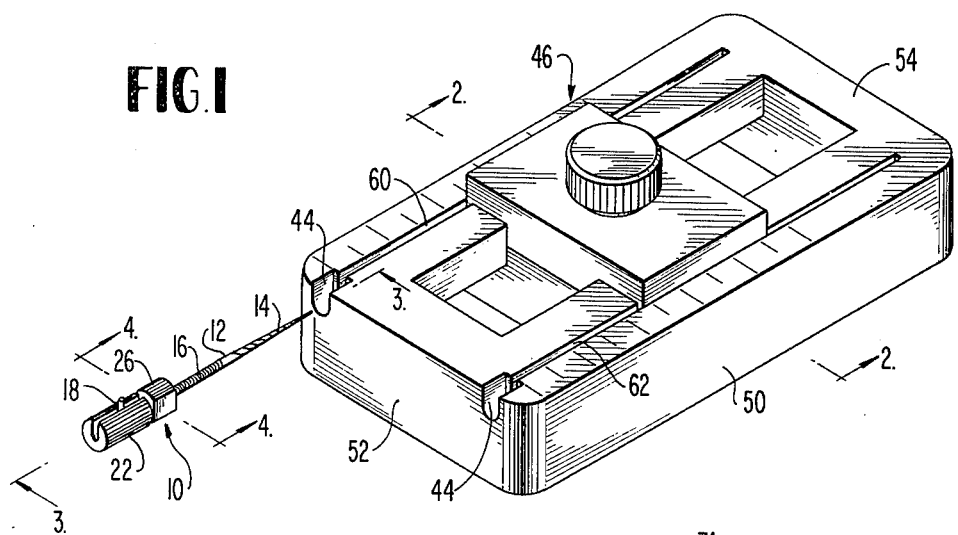
FIG. 1 is a perspective view of the endodontic instrument and adjusting tool according to the present invention.

Referring now to the drawings in detail, the endodontic instrument according to the present invention is indicated generally by the reference numeral 10 and includes a root canal file 12 having a working end in the form of a spiraled, tapered knife portion 14 and a cylindrical shaft or body portion 16 terminating at the end opposite the knife in a right angular portion 18. Formed on the body 16 of the file 12 are a plurality of closely spaced annular, shallow grooves which extend from adjacent the right angle portion 18 to the tapered knife portion 14. In practice, the shaft 16 may be within the range of 0.75 mm to 1.0 mm in diameter, with four grooves per millimeter formed therein.

Figure 4:
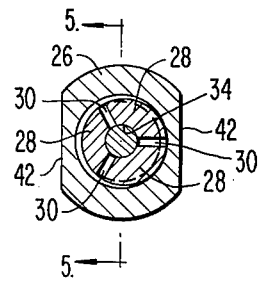
FIG. 4 is an enlarged sectional view taken on line 4—4 of FIG. 1.
Figure 3:
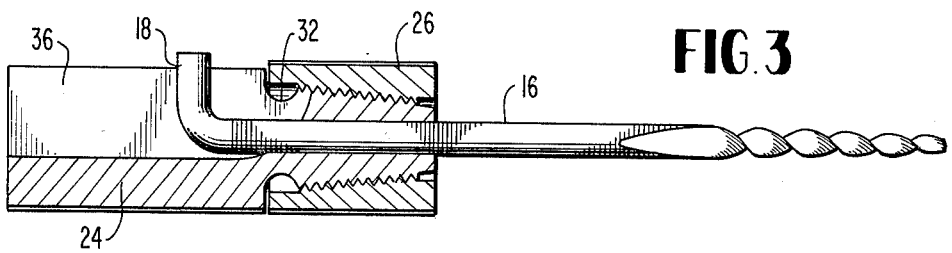
FIG. 3 is an enlarged fragmentary view taken on line 3—3 of FIG. 1.
Figure 5:
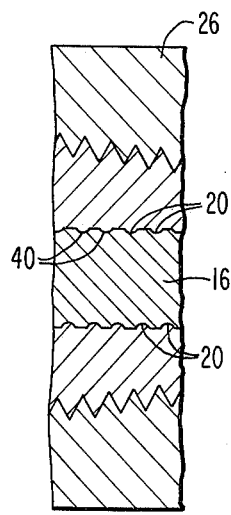
FIG. 5 is a further enlarged fragmentary view of a portion of the structure shown in FIG. 3.
Figure 6:
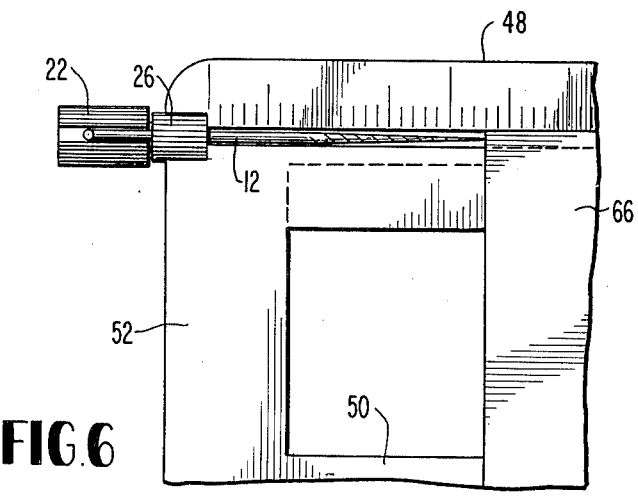
FIG. 6 is a top plan view of a portion of the structure shown in FIG. 1 with the instrument mounted in the tool.

The file 12 is supported in a handle 22 consisting of a cylindrical body portion 24 and having longitudinal scoring formed in its outer surface to provide a more positive grip. One end of the handle 22 is in the form of a chuck consisting of a nut 26 having tapered female threads formed therein adapted to be received on the tapered male threads on the jaws 28 formed by the three circumferentially spaced slits 30 as best seen in FIGS. 3 and 4. The jaws 28 are joined to the body 24 of handle 22 at a reduced diameter section formed by a circumferential, arcuate groove 32, which reduced section permits limited radial flexing of the jaws 28. As seen in FIGS. 4 and 5, a bore 34 extends axially through the portion of the handle 22 defined by the jaws 28, and communicates with a slot 36 having a width slightly greater than the diameter of the shaft 16 of the file, with the groove 36 extending outwardly to the surface of the handle to receive the right angle portion 18 of the file 12. A plurality of annular ridges 40 are formed in the inner surface of the bore 34 within the jaws 28, with the ridges 40 being adapted to fit within the grooves 20 as shown in FIG. 5 when the nut 26 is tightened on the handle forcing jaws 28 radially inward to firmly clamp the shaft 16 of the file 12. Jaws 28 are normally spaced apart a distance to permit through passage of the file 12 through the bore 34 when the nut 26 is loosened to permit the file to be easily positioned within the handle. However, when the nut is tightened only finger tight, engagement of the grooves 20 and ridges 40 positively retains the handle in position on the file regardless of the force exerted by use of the tool as when the tool tends to hang in a root canal and is forced inward or outward by pushing or pulling on the handle 22.

The nut 26 is formed with flat surfaces 42 on two sides thereof, with the surfaces 42 being parallel to one another and adapted to be snugly received between the opposed parallel walls of a substantially U-shaped recess 44 in an end surface of the tool assembly 46. The tool assembly comprises a generally rectangular body member formed from a dimensionally stable material and consisting of a pair of side beams 48, 50 retained in parallel spaced relation by integrally formed end members 52, 54. Beams 48, 50 are formed with inwardly directed, opposed shoulders 56, 58, respectively, which extend their full length and act as a guide for an adjustable stop assembly more fully described hereinbelow.

The beams 48, 50 are formed with elongated, narrow grooves 60, 62 respectively in their upper surface, with the grooves 60, 62 opening one into each of the two U-shaped recesses 44 in the end of the assembly. The grooves 60, 62 have a transverse dimension sufficient to receive the root canal file 12 when the nut 26 of the chuck assembly is positioned within one of the recesses 44. The top surfaces of the beams 48, 50 each have a scale thereon, preferably calibrated in millimeters and extending along the grooves 60, 62 from a position adjacent the shoulder defined by the intersection of the end wall of the U-shaped recesses 44 and the respective elongated grooves 60, 62. The grooves 60, 62 are of slightly different transverse dimension, each being adapted to snugly receive a standard sized file.

Figure 2:
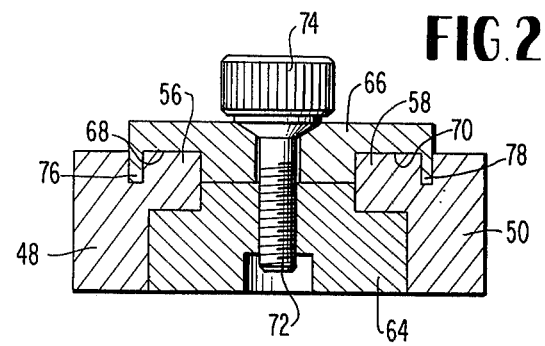
FIG. 2 is an enlarged sectional view taken on line 2—2 of FIG. 1.

As shown in FIGS. 1 and 2, the slide assembly consists of a generally rectangular guide block 64 adapted to be slidably received between the beams 48, 50, with a pair of recesses in the top surface of the block 64 receiving the shoulders 56, 58 on the respective beams. A second generally rectangular member 66 having a pair of parallel grooves 68, 70 formed therein is mounted on the guide block 64 by a bolt 72 having a knurled head 74 adapted to be manually turned to tighten or loosen the blocks 64, 66 together and thereby clamp the shoulders 56, 68. The flange portions 76, 78 outboard the respective recesses 68, 70 are adapted to fit snugly within the respective grooves 60, 62 to act as a stop member for the end of the root canal files 12 when the assembly clamped together by the bolt 72.

To position the root canal 12 in the handle 22, with the desired length of the file projecting from the end of the nut 26, the slide assembly on the tool is positioned relative to the scale on one of the beams 48, 50 and the bolt tightened by turning the knurled head 72. The chuck nut 26 is then positioned within the appropriate U-shaped recess 44, with the flat surfaces 42 fitting snugly within the opposed parallel sides of the recess and with the nut 26 loose on the handle 22. The angle-portion 18 of the root canal file 12 is then manually engaged and the file telescoped through the chuck until the end thereof abuts one of the flanges, for example, flange 76 within the groove 60. Placing one finger on top of the nut 26 to hold it within the U-shaped recess 44, the handle 22 can then be manually rotated to tighten the nut 26 and thereby firmly chuck the shaft 16 of the root canal file within the jaws 28. Since the shallow recesses 20 on the shaft of the root canal file and the ridges 40 on the inner surface of the jaws 28 will interlock and prevent relative axial movement between the handle 24 and the file 28 slightly before the nut 26 is completely tightened on the handle 22, the nut 26 will, upon continued rotation of the handle after this preliminary engagement, move slightly from the shoulder at the end of the U-shaped groove 44. However, since the grooves and ridges are shallow, only a small addition turn of the handle is required after this preliminary engagement to firmly tighten the nut, and the axial movement of the nut during this additional movement is compensated for in the scale on the top surface of the beams 48, 50. Thus, it is seen that the handle can be reliably and quickly attached to the root canal file, with the aid of the special tool, with precisely the correct amount of the file projecting from the end of the handle. The engagement between the handle and the file is positive, eliminating any possibility of undetected relative movement which could result in an improper length of file projecting from the handle.

It is contemplated that this invention may be employed to eliminate the conventional practice of providing a plurality of different lengths of file. This can be accomplished by providing flat surfaces on the handle 22, with these flat surfaces corresponding to the surfaces 42 on the chuck nut 26. In this embodiment, either the handle 22 or the nut 26 would be positioned within the U-shaped recess 44, and the root canal file would be telescoped through the assembly from the opposite direction. Thus, a conventional "long" file can be employed as a short file, with only a relatively short length of the file projecting from the handle assembly and without an objectionable length of the end of the shaft 16 projecting from the opposite end of the handle.

While I have disclosed and described a preferred embodiment of my invention, I wish it understood that I do not intend to be restricted solely thereto, but rather that I do intend to include all embodiments thereof which would be apparent to one skilled in the art and which, would be within the spirit and scope of my invention.

I claim:

1. An apparatus for determining the working length of a root canal file assembly of the type in which an elongated file has its shaft releasably mounted in a chuck of a handle assembly adapted to clamp the shaft in any desired position, said chuck including a nut threaded onto movable jaws of the handle assembly and operable to clamp and unclamp said shaft, the improvement wherein said apparatus comprises a body member, a measuring scale fixed on said body member, stop means mounted on said body member for movement along said scale, means releasably fixing said stop means in any desired position of adjustment along said scale, an elongated groove in said body and extending along said scale from said shoulder means, said groove being dimensioned to receive said root canal file therein, and jig means on said body for receiving said nut and cooperating therewith to prevent rotation thereof upon rotation of said handle assembly, said jig means including shoulder means for fixing the position of said nut relative to said scale and in alignment with said stop.

2. The apparatus as defined in claim 1 wherein said stop means includes abutment means projecting into said groove in position to be engaged by the end of a root canal file positioned therein.

3. An apparatus for determining the working length of a root canal file assembly of the type in which an elongated file has its shaft releasably mounted in a chuck of a handle assembly adapted to clamp the shaft in any desired position, said chuck including a nut threaded onto movable jaws of the handle assembly and operable to clamp and unclamp said shaft, the improvement wherein said apparatus comprises a body member, a measuring scale fixed on said body member, stop means mounted on said body member for movement along said scale, means releasably fixing said stop means in any desired position of adjustment along said scale, and jig means on said body for receiving said nut and cooperating therewith to prevent rotation thereof upon rotation of said handle assembly, said jig means including shoulder means for fixing the position of said nut relative to said scale and in alignment with said stop, a substantially U-shaped recess formed in said body member and having two substantially parallel flat surfaces adapted to engage flat surfaces on said nut to prevent rotation thereof.

* * * * *